(12) United States Patent
Epstein et al.

(10) Patent No.: US 6,733,472 B1
(45) Date of Patent: May 11, 2004

(54) SEALANT APPLICATOR TIP AND APPLICATION METHOD

(75) Inventors: Gordon Howard Epstein, Fremont, CA (US); Mitchell E. Levinson, Pleasanton, CA (US); Richard K. Spero, Brentwood, CA (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/375,755

(22) Filed: Aug. 18, 1999

Related U.S. Application Data

(63) Continuation-in-part of application No. 09/315,702, filed on May 20, 1999, which is a continuation-in-part of application No. 09/037,160, filed on Mar. 9, 1998, now Pat. No. 6,063,055, which is a continuation-in-part of application No. 08/946,364, filed on Oct. 7, 1997, now Pat. No. 6,007,515, which is a continuation-in-part of application No. 08/838,078, filed on Apr. 14, 1997, now Pat. No. 6,331,172, which is a continuation-in-part of application No. 08/839,614, filed on Apr. 14, 1997, now Pat. No. 5,971,956.
(60) Provisional application No. 60/096,940, filed on Aug. 18, 1998.

(51) Int. Cl.[7] .................................................. A61M 1/00
(52) U.S. Cl. ............................ 604/30; 604/83; 604/89; 604/35; 137/454.2; 137/625.4; 606/92; 606/213; 251/319; 251/352; 222/145.5; 222/145.2; 222/148
(58) Field of Search ......................... 604/83, 191, 181, 604/82, 173, 187, 36, 266, 89, 35, 902, 43, 27, 28, 30, 90, 46, 48, 39, 268, 167.01, 236, 275, 218; 606/214, 215, 92–94, 213; 222/135, 136, 145.5, 137, 145.2, 148, 387, 145.1, 145.8, 145.7; 251/319, 352; 137/454.2, 625.4

(56) References Cited

U.S. PATENT DOCUMENTS

| 2,812,765 A | 11/1957 | Tofflemire |
| 3,188,056 A | 6/1965 | Trumbull et al. |
| 3,828,980 A | 8/1974 | Creighton et al. |

(List continued on next page.)

FOREIGN PATENT DOCUMENTS

| DE | 4208344 | 9/1993 |
| EP | 0156098 | 12/1984 |
| EP | 0315222 | 12/1984 |
| EP | 0634140 | 9/1993 |
| WO | WO 9619940 | 4/1996 |

OTHER PUBLICATIONS

International Search Report dated Apr. 10, 2000 regarding application PCT/US99/18868.

*Primary Examiner*—Brian L. Casler
*Assistant Examiner*—Cris L. Rodriguez
(74) *Attorney, Agent, or Firm*—Jeffrey C. Nichols; Mark J. Buonaiuto; Francis C. Kowalik (57) ABSTRACT

Multipurpose fluid applicators and applicator tips, particularly suitable for surgical purposes, are disclosed. The applicators and applicator tips are specifically designed for dispensing various combinations of sterile pressurized gas, suction, irrigation and sealant agents, including a mixed liquid sealant agent. Preferred embodiments employ a dual-acting valve selectively to control the flow of gas or suction which valve is capable of simultaneously varying flow from a source and the venting of that flow to atmosphere.

13 Claims, 13 Drawing Sheets

U.S. PATENT DOCUMENTS

| | | |
|---|---|---|
| 4,040,420 A | 8/1977 | Speer |
| 4,067,479 A | 1/1978 | Moline |
| 4,083,474 A * | 4/1978 | Waite et al. ................. 222/145 |
| 4,109,653 A | 8/1978 | Kozam et al. |
| 4,325,913 A | 4/1982 | Wardlaw |
| 4,359,049 A | 11/1982 | Redl et al. |
| 4,445,517 A | 5/1984 | Feild |
| 4,519,385 A | 5/1985 | Atkinson et al. |
| 4,631,055 A | 12/1986 | Redl et al. |
| 4,735,619 A | 4/1988 | Sperry et al. |
| 4,776,840 A | 10/1988 | Freitas et al. |
| 4,842,581 A | 6/1989 | Davis |
| 4,874,368 A | 10/1989 | Miller et al. |
| 4,978,336 A | 12/1990 | Capozzi et al. |
| 4,979,942 A | 12/1990 | Wolf et al. |
| 5,045,055 A | 9/1991 | Gonser et al. |
| 5,186,714 A | 2/1993 | Boudreault et al. |
| 5,226,877 A | 7/1993 | Epstein |
| 5,304,165 A | 4/1994 | Haber et al. |
| 5,310,091 A | 5/1994 | Dunning et al. |
| 5,328,459 A | 7/1994 | Laghi |
| 5,332,157 A * | 7/1994 | Proctor ........................ 239/304 |
| 5,395,326 A | 3/1995 | Haber et al. |
| 5,405,607 A | 4/1995 | Epstein |
| 5,447,494 A | 9/1995 | Dorsey, III |
| 5,474,540 A | 12/1995 | Miller et al. |
| 5,571,081 A | 11/1996 | Adhoute |
| 5,585,007 A | 12/1996 | Antanavich et al. |
| 5,605,255 A | 2/1997 | Reidel et al. |
| 5,611,462 A * | 3/1997 | Barkes ........................ 222/134 |
| 5,648,265 A | 7/1997 | Epstein |
| 5,749,968 A | 5/1998 | Melanson et al. |
| 5,887,755 A | 3/1999 | Hood, III |
| 5,971,956 A * | 10/1999 | Epstein .................... 137/625.4 |
| 5,989,215 A | 11/1999 | Delmotte et al. |
| 6,007,515 A * | 12/1999 | Epstein et al. .............. 604/131 |
| 6,047,861 A * | 4/2000 | Vidal et al. .................. 222/137 |
| 6,063,055 A * | 5/2000 | Epstein et al. .............. 604/191 |
| 6,331,172 B1 * | 12/2001 | Epstein et al. .............. 604/191 |

\* cited by examiner

SEALANT APPLICATOR TIP AND APPLICATION METHOD

CROSS REFERENCE TO RELATED APPLICATIONS

The present application claims priority from U.S. provisional patent application serial No. 60/096,940 filed on Aug. 18, 1998. The present application also is a continuation-in-part of co-pending U.S. patent application Ser. No. 08/838,078 filed on Apr. 14,1997, now U.S. Pat. No. 6,331,172, and a continuation in part U.S. patent application Ser. No. 08/839,614, filed on Apr. 14, 1997, now U.S. Pat. No. 5,971,956, and a continuation-in-part of U.S. patent application Ser. No. 08/946,364, filed on Oct. 7, 1997, now U.S. Pat. No. 6,007,515, and a continuation-in-part of U.S. patent application Ser. No. 09/037,160, filed on Mar. 9, 1998, now U.S. Pat. No. 6,063,055, all naming Gordon H. Epstein as first named inventor. Also, the present application is a continuaton-in-part of U.S. patent application Ser. No. 09/315,702, filed on May 20, 1999, naming Mitchel Levinson as first named inventor. The disclosures of the aforementioned United States patent applications are hereby incorporated by reference In their entirety herein.

STATEMENT REGARDING FEDERALLY SPONSORED RESEARCHER DEVELOPMENT (Not Applicable)

BACKGROUND OF THE INVENTION

1. Field of the Invention

The present invention relates to an apparatus and method for applying component parts of a sealant which when mixed transforms from a fluidic state to a non-fluidic state. In particular but not exclusively, the present invention is directed to an apparatus and process in which sealant components are mixed prior to being applied to biological tissue to effect hemostasis or achieve other therapeutic results.

2. Description of Related Art Including Information Disclosed under 37 CFR 1.97 and 37 CFR 1.98

Use of tissue sealants and other biological materials is an important emerging surgical technique, well adapted for the operating room or field environments such as the doctor's office or mobile medical units. In addition, the application of such sealants while performing or as necessary to perform minimimally invasive surgery reduces or eliminated the traditional problems associated with more invasive types of procedures. Preferred sealants include fibrin sealants which are formed from blood plasma components and comprise, on the one hand, a first component containing fibrinogen and Factor XIII and on the other hand a second component which usually includes thrombin, and calcium ions.

The fibrinogen is capable of a polymerizing and being cross-linked to form a solid fibrin clot when the components are mixed. The necessary additional factors to simulate relevant portions of the natural blood coagulation cascade are suitably distributed between the fibrinogen and thrombin components.

High levels of protection against transmission of infections or induction of immunological reactions can be assured by using an autologous or single-donor source for both components. Such sealants are highly effective, are biologically degraded without residue and may promote wound healing.

Depending upon the potency of the particular formulations employed, coagulation of the sealant may take place very rapidly, yielding a gel within perhaps 10 or 20 seconds after mixing of the two components. Though often very desirable for surgical reasons, such fast-acting properties present potential problems of fouling or clogging. These problems must be overcome in devising suitable applicators, and methods of application.

A popular manually operable applicator for such two-component sealants employs a dual syringe construction wherein two syringes, connected by a yolce, each provide a reservoir for one of the components. In most prior devices, the sealant components are discharged in separate streams and mixed externally of the applicator. Such applicators are similar in principle to household epoxy glue applicators commonly available in hardware stores. Achieving effective mixing externally of the applicator is problematic.

In U.S. Pat. No. 5,266,877, and the above applications, the present inventor teaches various constructions of a dual syringe applicator wherein the fluid sealant components are mixed internally.

Antanavich et al. U.S. Pat. No. 5,585,007, whose disclosure and references are hereby incorporated herein by reference thereto, provides an extensive discussion of the literature relating to fibrinogen sealant preparation (column 1, line 20 to column 4, line 62) and applicators column 4 line 62 to column 5, line 14), as well as a bibliography, (columns 6–10) and is a helpful guide to the teachings of prior workers in the field.

Though a superior quality sealant can be obtained, a difficulty with internal mixing is that the coagulating nature of the sealants causes the discharge opening or openings of an application device to become clogged so that flow out of the applicator slows down or stops.

While the above-referenced copending applications disclose effective clearing methods, difficulties may occur if the mixing pathway to be cleared has an extended length such as might be required to reach an unexposed location or work site.

There is accordingly a need for a sealant applicator and method that can be used to reach an unexposed location and that is capable of being rapidly unclogged without disassembly of the applicator.

SUMMARY OF THE INVENTION

The present invention solves this problem by providing an applicator tip comprising a mixing chamber communicating with two or more reservoirs which can effectively deliver mixed multiple sealant components to a remote work area and is capable of being unclogged without removing or relocating the applicator tip or by dispersing unwanted clots into the application environment.

The present invention also assures that an effective sealant composition reaches the area of application because the sealant components are actively mixed in close proximity to the applicator outlet while also providing for means of removal of coagulated sealant from the applicator tip.

Preferably, although not necessarily, the sealant is a biological sealant, for example a tissue adhesive, and the area of application is a biological tissue subject to surgery. The sealant components can comprise a first, structural component capable of gelling, and preferably of solidification and a second, activation component which activates such gelling and, optionally, solidification. More preferably, the sealant is a tissue sealant and the first component comprises fibrinogen and the second component comprises, or can generate a fibrinogen activator, especially thrombin or an equivalent thereof.

The invention also provides a novel surgical method of applying sealant to unexposed or internal biological surfaces, e.g. human or animal anatomical surfaces, that are accessible to a remote application devices, such as the ones disclosed in aforementioned patent applications. The use of a remote mixing chamber, which receives a flow of multiple sealant components and mixes the sealant components at the distal end of the applicator, allows the distal end of the applicator to apply a mixed sealant a work site.

BRIEF DESCRIPTION OF THE DRAWINGS

One way of carrying out the invention is described in detail below with reference to the drawings which illustrate one or more specific embodiments of the invention and in which:

FIG. 14d is a cross sectional view along lines 14d—14d of FIG. 14a.

DESCRIPTION OF THE PREFERRED EMBODIMENTS

Figure 1:
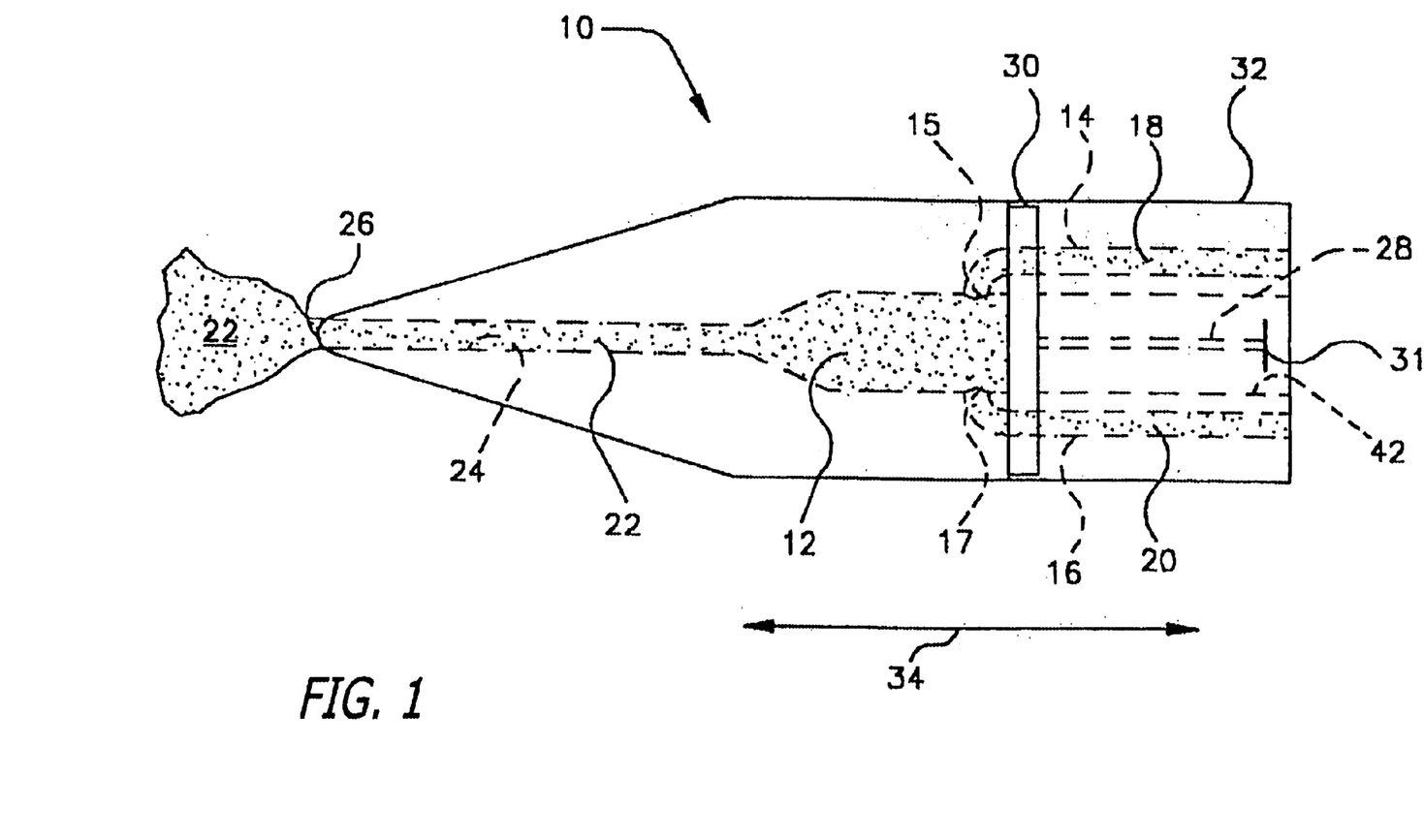
FIG. 1 is a top plan view of a first embodiment of a sealant applicator tip according to the present invention.
Figure 2:
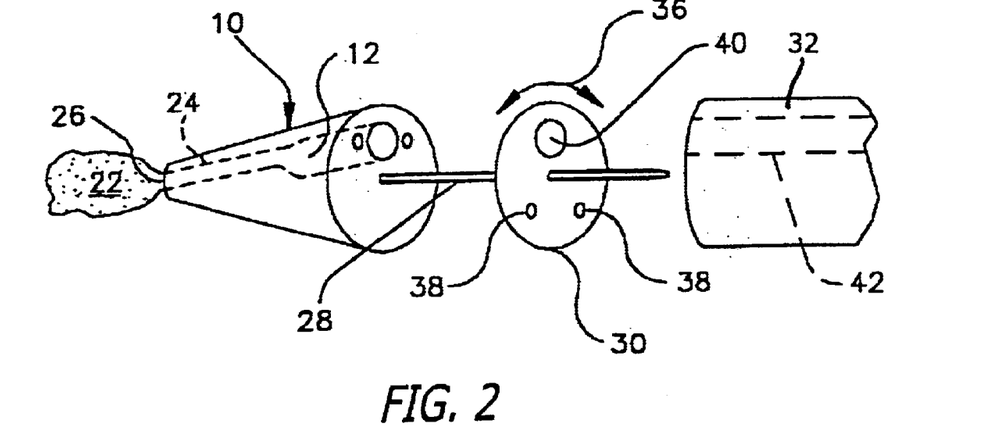
FIG. 2 is a perspective view of the FIG. 1 embodiment showing a rotatable plate in a first position.
Figure 3:
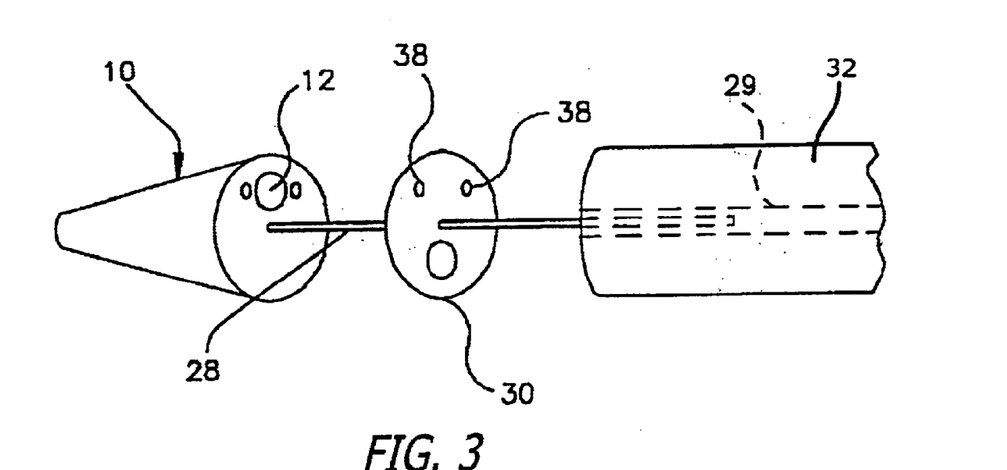
FIG. 3 is a perspective view of the FIG. 1 embodiment showing a rotatable plate in a second position.

Referring now to FIGS. 1–3, a sealant applicator tip 10, for use with a sealant application instrument (FIGS. 14a–c) is illustrated. Tip 10 is generally conical in shape and is configured to have an internal mixing chamber 12. Mixing chamber 12 communicates with a pair of conduits 14 and 16 which each supply a sealant agent 18 or 20, respectively, for internal mixing in mixing chamber 12. Preferably, agents 18 and 20 are those disclosed in the aforementioned patent applications, and are manually dispersed under pressure applied by the user from reservoirs (not shown).

As previously discussed, once mixed, agents 18 and 20 provide a sealant 22 which is used for application to a remote area. Sealant 22 travels through an application conduit 24 which is configured to deliver sealant 22 to an application opening 26.

The coagulating nature of the sealant sometimes causes the discharge opening or openings of an application device to become clogged so that flow out of the applicator slows down or stops.

Thus, it is one aspect of the present invention to provide for retrograde clearing of the mixing chamber while also limiting the flow of agents 18 and 20 during such clearing.

Tip 10 is mounted to a pin 28 which is slidably received within an opening 29 (FIG. 3). As illustrated in FIGS. 1–3, to provide an extended reach, the application device (see FIGS. 14a–c) is equipped with an elongated shaft 32 having applicator tip 10 removably mounted to the distal end of the device.

As an alternative or as a supplement conduits 14 and 16, are used to deliver an irrigation fluid and/or pressurized gas as well as agents 18 and 20.

Although described in the context of an applicator with an extension tip, it will be understood that the sealant valving and clearing mechanisms disclosed herein can also be embodied in other applications such as those having relatively shorter tips, as disclosed in the above applications.

To facilitate the clearing of mixing chamber 12, a circular plate 30 is rotatably mounted on pin 28. Plate 30 is located between tip 10 and shaft 32 and is rotated either manually by the user or is rotated through the incorporation of a remotely positioned actuating device, such as a trigger 150 (see FIG. 14a).

Figures 14A, 14B, 14C:
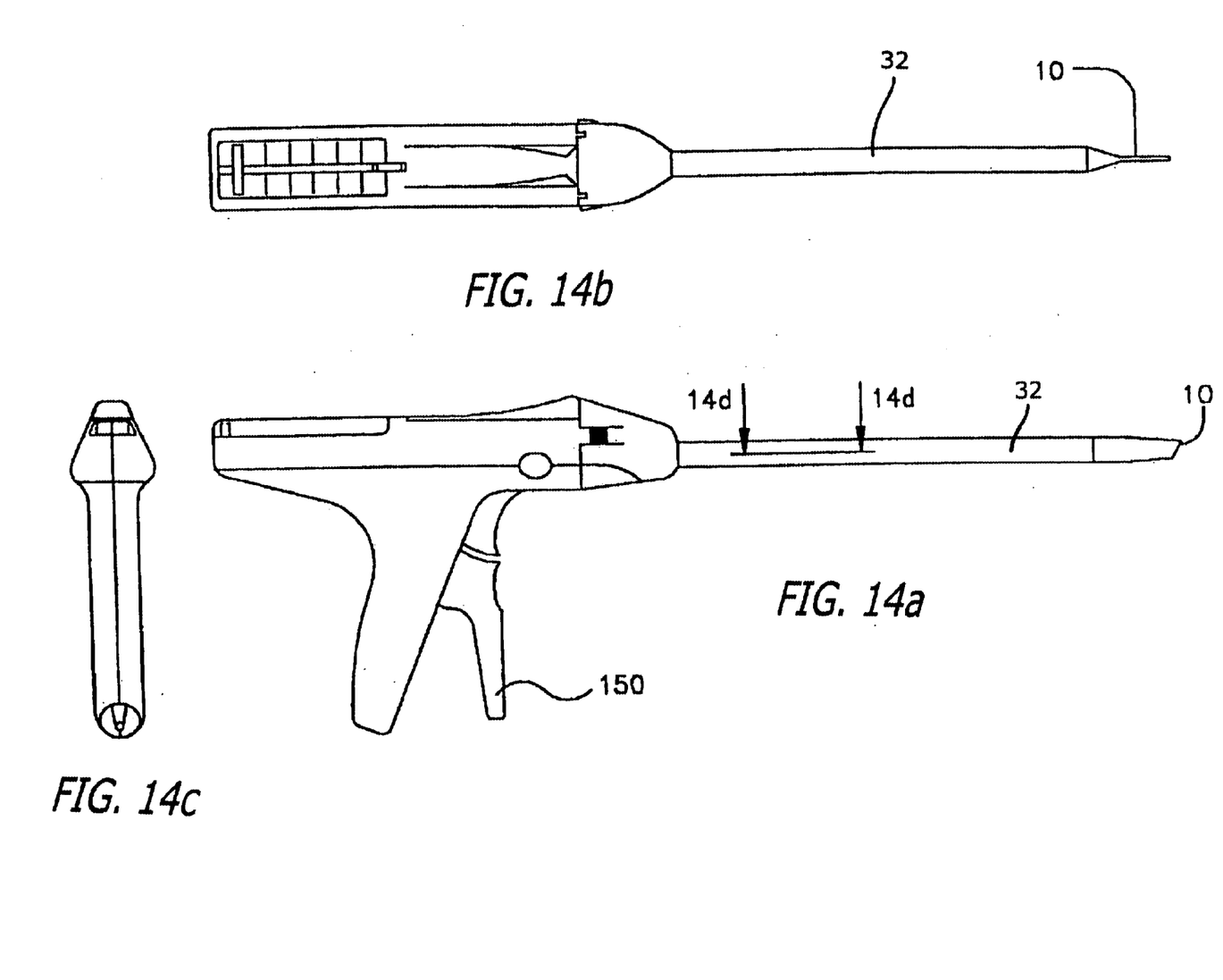
FIGS. 14a–c illustrate a sealant application instrument for use with the present invention.

As an alternative, pin 28 and accordingly plate 30 is rotated from a position remote from tip 10. This rotation can also be facilitated through trigger 150.

Tip 10 is slidably mounted to shaft 32 via pin 28. Pin 28 slides into and away from shaft 32. This allows tip 10 to be moved in the directions of arrow 34 and to the positions illustrated by FIGS. 1–3.

Referring now in particular to FIGS. 2 and 3, circular plate 30 is capable of being rotated in the directions indicated by arrow 36. Circular plate 30 has a pair of openings 38 and an opening 40. Openings 38 are configured to align with conduits 14 and 16 when circular plate 30 is in the position depicted by FIG. 3. Opening 40 is configured to align with mixing chamber 12 when circular plate 30 is in the position depicted by FIG. 2. In addition, opening 40 is larger than openings 38. In the preferred embodiment, opening 40 is as large as mixing chamber 12. The larger size of opening 40 helps facilitate the removal of clotted material from mixing chamber 12.

If desired, conduits 14 and 16, and openings 38 can be radially offset to avoid cross contamination as plate 30 rotates.

Accordingly, and as can be seen by FIGS. 1–3, to remove coagulated sealant that has partially or totally clogged conduit 22, a user manipulates plate 30 to the position illustrated by FIG. 2. In this position conduits 14 and 16 are blocked off by circular plate 30 while mixing chamber 12 is aligned to opening 40 which allows a suction force to be applied to mixing chamber 12 via conduit 42.

Thus, circular plate 30 may be rotated to allow for application of sealant 22 or removal of coagulated sealant from mixing chamber 12.

Once circular plate 30 is placed into the desired position, the user then will either apply sealant 22 or remove coagulated sealant from mixing chamber 12.

To facilitate removal of coagulated sealant a suction force is applied to mixing chamber 12 via a suction conduit 42. Accordingly, retrograde clearing of mixing chamber 12, application conduit 24 and opening 26 is possible. Thus, the present invention allows a user to clear applicator tip 10 should it become clogged. This feature is of particular importance especially if tip 10 becomes clogged during a surgical procedure. In accordance with the present invention the user can clear the clogged passage in a quick and easy manner convenient to the user. In addition, retrograde clearing prevents coagulated sealant from being dispersed into the application area.

Tip 10 may also be completely removed to insert another tip which has different features, such as, a more elongated nose shape, a larger or smaller application opening, an angular configuration to the distal end of tip 10 or any other configuration which would vary the application of sealant 22. In addition, tip 10 may even be disposed being replaced with a new tip, for example, for each patient.

Optionally, to prevent inadvertent removal of tip 10, pin 28 is equipped with a retaining device 31. Retaining device 31 prevents pin 28 from being completely removed from shaft 32. As an example, retaining device may be an end stop with a larger diameter than opening 29.

In addition, the movement of tip 10 away from shaft 32 may also be limited by a locking mechanism, such as a spring loaded ball bearing device, which is received into recesses positioned along opening 29 and can lock tip 10 into position at differing spacings from shaft 32.

A preferred external configuration of tip 10 is that of a blunt pencil tip, as shown, facilitating access to internal locations of a treatment subject, providing a manipulable dispersing tip and avoiding tissue damage by sharp or bulky protuberances.

In addition and as an alternative embodiment, and when retrograde suction is applied to mixing chamber 12, conduits 14 and 16 are equipped with one way flap valves 15 and 17 respectively (see the dashed lines in FIG. 1). Flap valves 15 and 17 prevent flow from mixing chamber 12 back into conduits 14 and 16. In this embodiment retrograde suction may also be applied to conduits 14 and 16 which will draw back sealant agents 18 and 20 but not any coagulated or mixed sealant 22. Thus, and in this embodiment, retrograde suction may be applied to remove coagulated sealant 22 without drawing sealant agent 18 and 20 with it.

In yet another embodiment, valves 15 and 17 are used to completely close off conduits 14 and 16 and are actuated to close when retrograde suction is applied to mixing chamber 12.

Alternatively, conduits 14 and 16, which in accordance with the co-pending and commonly owned patent applications, are flexible and capable of being easily manipulated. In this embodiment, the flexible nature of conduits 14 and 16 allows for them to be pinched or easily constricted to prevent flow therethrough. Accordingly, conduits 14 and 16 are pinched to prevent flow of sealant agents 18 and 20 when retrograde suction is applied to mixing chamber 12.

Such pinching of conduits 14 and 16 can be performed at either the distal or proximal end of an application device, such as the one depicted in FIG. 14a and the above mentioned copending patent applications.

Pinching of conduits 14 and 16, at either the proximal or distal end of the application device, in addition to sealing off conduits 14 and 16 for retrograde clearing, will also provide a hydraulic force or surge through conduits 14 and 16. This will force out a small amount of agents 18 and 20, prior to the application of retrograde suction.

This forcing of a small amount of agents 18 and 20 out of conduits 14 and 16 will assist in dislodging coagulated sealant 22 from the openings of conduits 14 and 16 communicating with mixing chamber 12.

Locating the mechanism for the pinching of conduits 14 and 16 at the proximal end of the application device will provide the user with an ergonomic means for closing off of conduits 14 and 16.

Accordingly, a trigger manipulated device can be ergonomically placed for the user to pinch off conduits 14 and 16 and create a hydraulic force of sealants 18 and 20 for dislodging any coagulated mixed sealant 22.

Figure 14D:
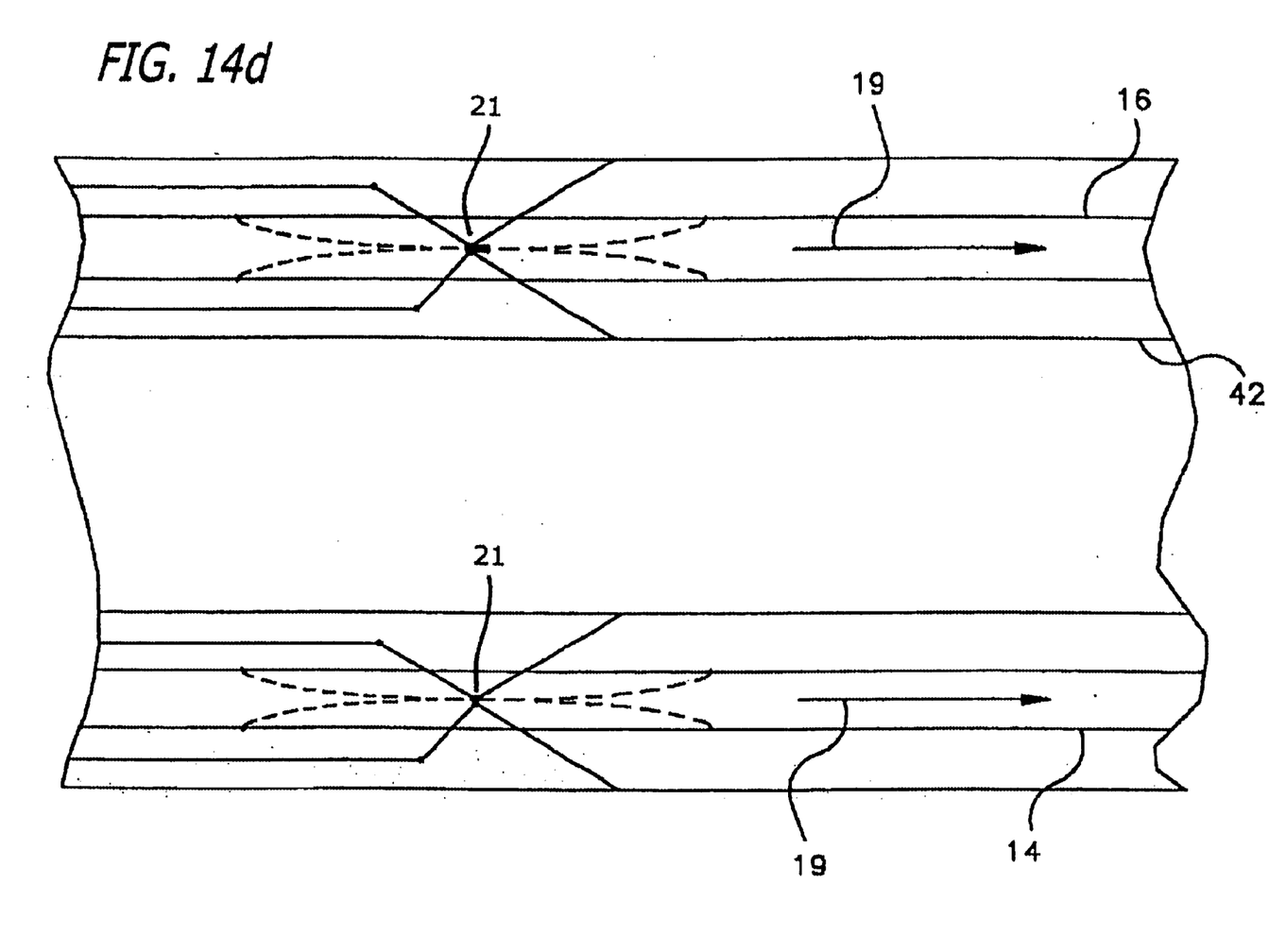

As illustrated in FIG. 14d a pair of flexible hinges 21 manipulated by a user activated trigger can effectively pinch conduits 14 and 16 into the position illustrated by the dashed lines. Such manipulation creates a force of sealant 18 and 20 in the direction of arrows 19.

As an alternative, hinges 21 can be replaced by, a slidable roller, a slidable shuttle having an opening that reduces in size and effectively pinches off conduits 14 and 16, or any other mechanical equivalent that can pinch off conduits 14 and 16 through the use of user applied force which returns to its unconstricting position after the force is removed.

In addition, such placement proximal placement of the pinching mechanism also limits the amount of working parts at the distal end of the device, which is generally inserted into hard to reach areas and, accordingly, is small in its overall size.

Figure 4:
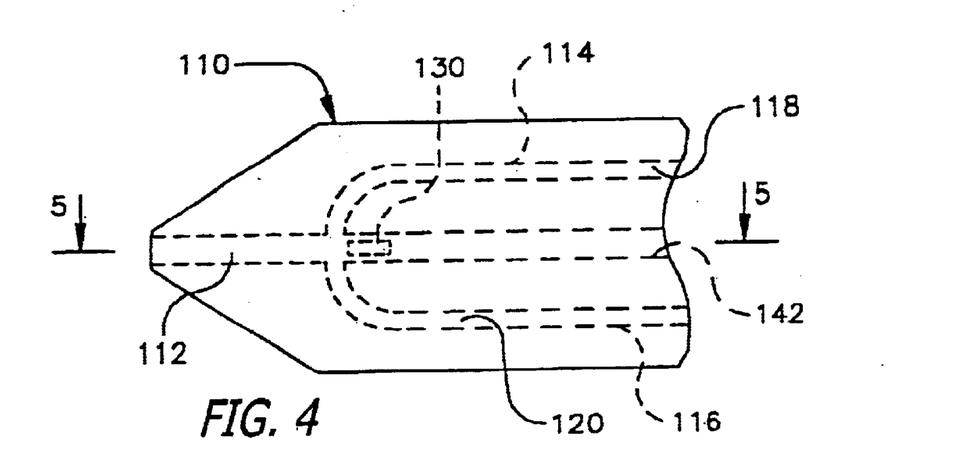
FIG. 4 is a top plan view of a second embodiment of the present invention.
Figure 5A:
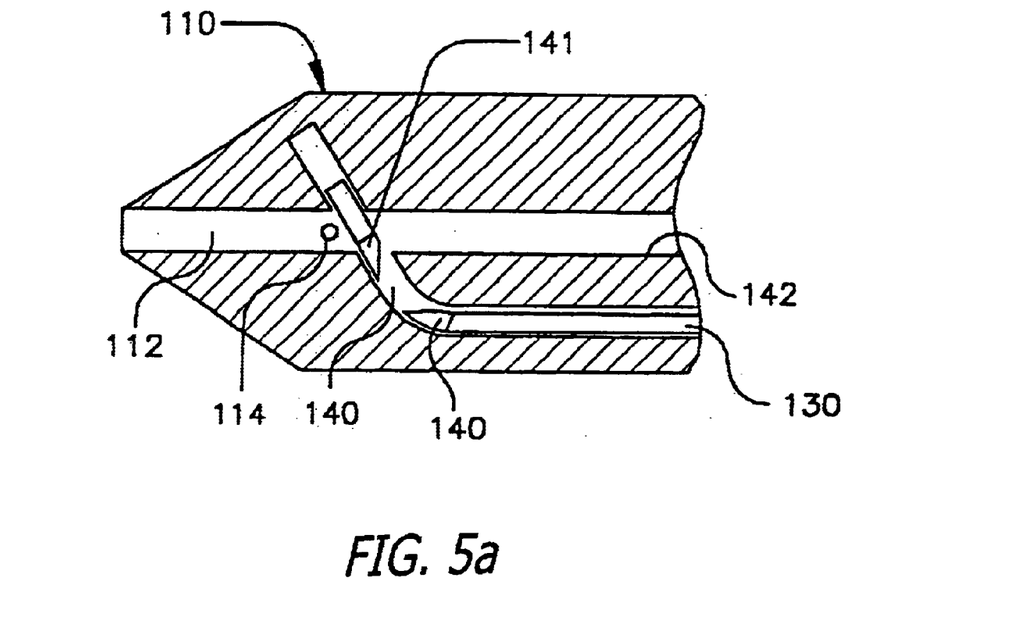
FIG. 5a is a cross sectional view along the lines 5—5 of FIG. 4 in a first position.
Figure 5B:
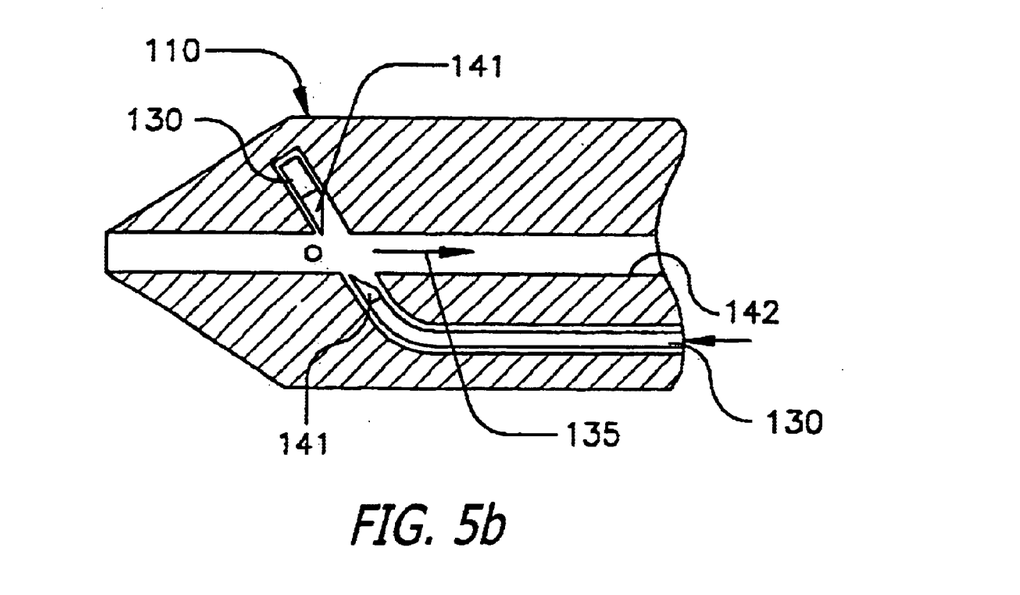
FIG. 5b is a cross sectional view along the lines 5—5 of FIG. 4 in a second position.
Figure 6:
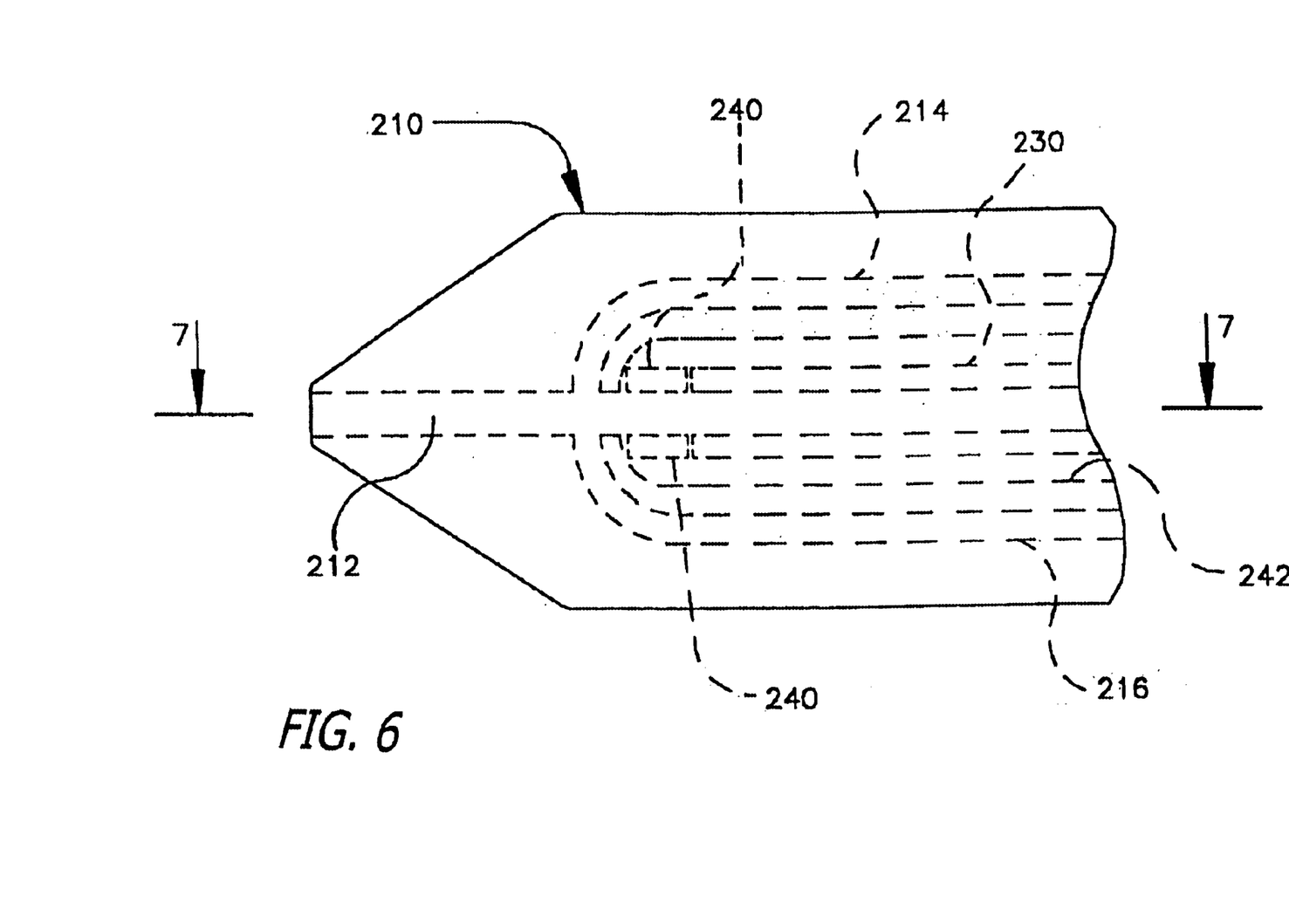
FIG. 6 is a top plan view of a third embodiment of the present invention.

Referring now to FIGS. 4, 5a and 5b another alternative embodiment of the present invention is illustrated. In this embodiment, components and/or parts performing analogous or similar functions to those in FIGS. 1–3 are numbered in increments of 100. Here communication of mixing chamber 112 with conduit 142 is limited by a shuttle 130. Shuttle 130 is made of flexible material (such as plastic or metal) and is slidably positioned within tip 110 and is manipulated by the user at a convenient location remote to applicator tip 110.

Shuttle 130 is configured to have an opening 140 which when it is in the position illustrated by FIG. 5b retrograde clearing, as previously discussed, of mixing chamber 112 is possible. In the preferred embodiment, opening 140 is at least as large as the opening into mixing chamber 112. However, opening 140 may be larger than the opening to mixing chamber 112. After clearing coagulated sealant from mixing chamber 112, shuttle 130 is then moved into the positioned illustrated by FIG. 5a. Opening 140 of shuttle 130 is equipped with a pair of blades 141 positioned on either end of opening 140. Thus, as shuttle moves from the positions depicted in FIGS. 5a and 5b any coagulated sealant is sheared off by blades 141 and suctioned out through conduit 142.

To facilitate the movement of shuttle 130 back into the position illustrated by FIG. 5a, a spring actuated trigger 150 (FIG. 14a) can be configured to manipulate the movement of shuttle 130. Therefore, the user need only to release the trigger and shuttle 130 moves back into the position illustrated by FIG. 5a.

Alternatively, the trigger movement of shuttle 130 may also be tied into the application of sealant 122 (application of sealants agents 118 and 120). In this variation the application of sealant 122 is caused by manipulating a trigger which simultaneously moves shuttle 130 into the position of FIG. 5a. Thus, as the user releases the trigger, application of sealant 122 stops and shuttle 130 moves into the position of FIG. 5b, and retrograde clearing is possible.

In addition, and as illustrated trigger 150 is remotely positioned with respect to applicator tip 10. Accordingly, the release of sealants 18 and 20, mixed sealant 22 and the retrograde clearing of tip 10 can be remotely controlled.

Moreover and as another alternative, a constant suction force can be applied to conduit 142 in the direction of arrow 135. Thus, and as discussed above, as the user releases the trigger, application of sealant 122 stops and shuttle 130 automatically moves into the position of FIG. 5b, and retrograde clearing is instantaneously initiated.

In summation, mixing chamber 112 is effectively blocked off from conduit 142 while conduits 114 and 116 are still in communication with mixing chamber 112. In this position agents 118 and 120 can now be supplied to mixing chamber 112 via positive pressure from conduits 114 and 116. This provides for turbulent mixing of the agents prior to application.

Referring now to FIGS. 6, 7a, 7b and 7c, yet another alternative embodiment of the present invention is illustrated. In this embodiment, components and/or parts performing analogous or similar functions are numbered in multiples of 100. Here retrograde clearing of mixing chamber 212 is limited by a silicon tube 240.

Figure 7A:
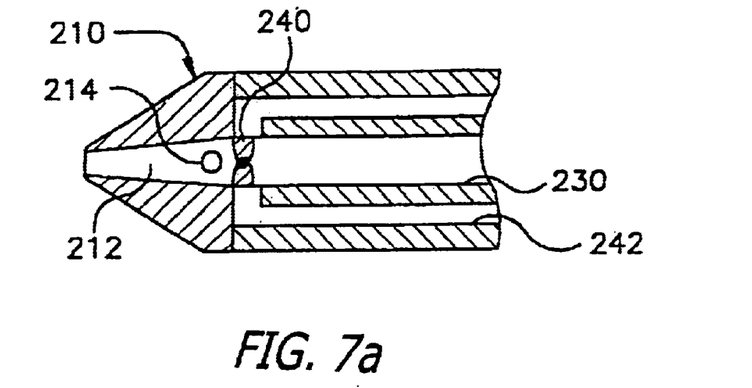
FIG. 7a is a cross sectional view along lines 7—7 of FIG. 6 in a first position.

Silicon tube 240 is attached to a conduit 230 at one end and mixing chamber 212 at the other end. Conduit 230 is position within a second conduit 242 which is larger in diameter than conduit 230.

The flexible nature of silicon tube 230 and the diameter of conduit 242 allows conduit 230 to be rotated in the direction indicated by arrow 234.

Figure 7B:
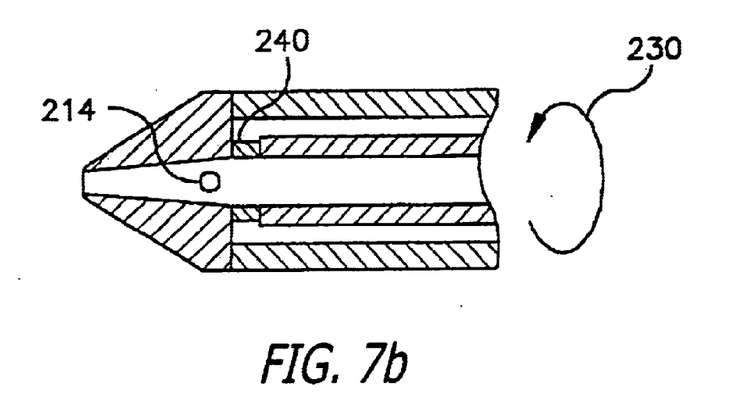
FIG. 7b is a cross sectional view along lines 7—7 of FIG. 6 in a second position.

Referring now to FIG. 7b, in this position conduit 230 and silicon tube 240 allow for retrograde clearing of mixing chamber 212. As conduit 230 is rotated, silicon tube 240 is twisted and conduit 230 is drawn closer to mixing chamber 212. Ultimately, silicon tube 240 is twisted until communication from conduit 230 to mixing chamber 212 is cut off. In this position agents 218 and 220 can now be supplied to mixing chamber 212 via positive pressure from conduits 214 and 216 to provide for turbulent mixing of the same prior to application.

When silicon tube 240 is in the position illustrated by FIG. 7b, conduits 214 and 216 are blocked off to prevent retrograde suction of sealant agents 218 and 220. Such blocking can be facilitated through the pinching of conduits 214 and 216.

Figure 7C:
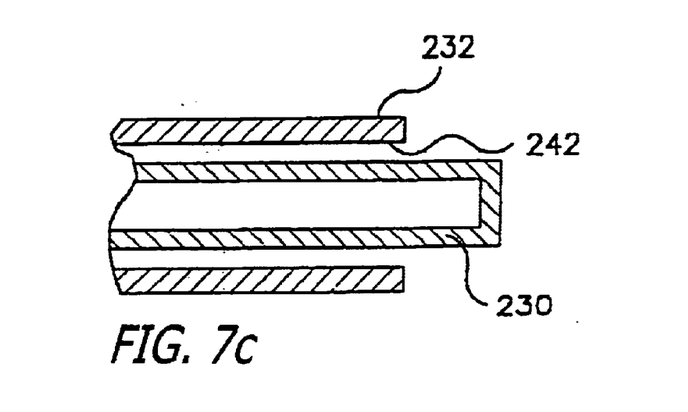
FIG. 7c is a cross sectional view of the FIG. 6 embodiment.

Referring now to FIG. 7c, the opposite end of shaft 232 is illustrated. Here conduit 230 extends outwardly from conduit 242 to provide for an extended surface to allow for the user to easily manipulate conduit 230.

The twisting of conduit 230 will create a torsional moment that, when conduit 230 is released, will cause silicon tube 240 to return to its untwisted position.

Alternatively, and in order to assist the user, conduit 230 can be configured to have a locking mechanism, such as a ratchet and pawl retaining device, or the equivalent thereof, to maintain silicon tube 240 in its twisted position.

Figure 8A:
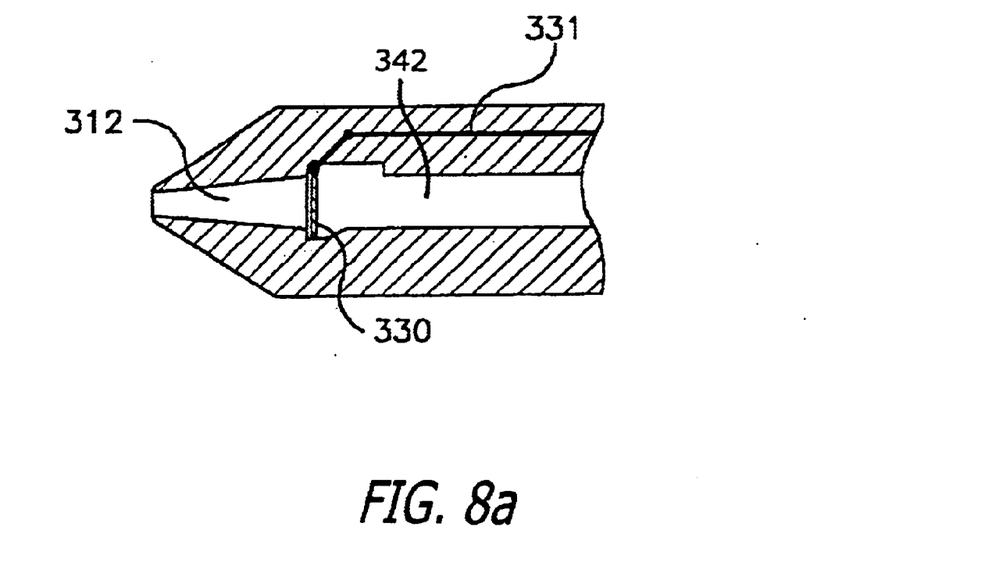
FIGS. 8a–b is a cross sectional view of a fourth embodiment of the present invention.
Figure 8B:
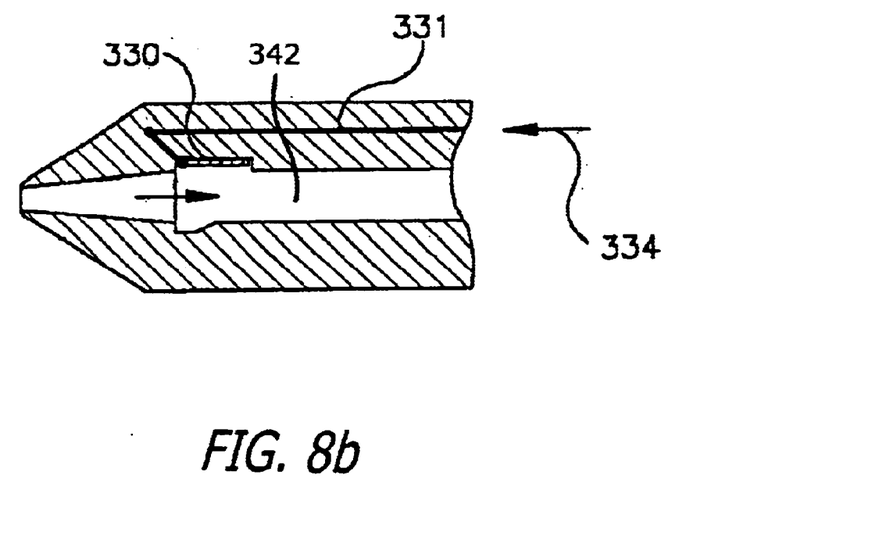

Referring now to FIGS. 8a and 8b yet another alternative embodiment of the present invention is illustrated. Here communication of mixing chamber 312 with conduit 342 is limited through the incorporation of a flap valve 330. Flap valve 330 is preferably constructed out of a stiff material such as hardened plastic or metal and opens and closes by manipulation of an actuating arm 331. The manipulation of actuating arm 331, as indicated by arrow 334, cause flap valve 330 to either open or close. Flap valve 330 is pivotally secured to the inner surface of conduit 342 through the use of a hinge or other equivalent mechanism.

Flap valve 330 is received into a recess in conduit 342 (as illustrated in FIG. 8b) when it is in its open position. The recessment of flap valve 330 assists in the unimpeded clearing of mixing chamber 312. As discussed above, the manipulation of valve 330 can be associated with the application of sealant 22 (ie. use of a trigger mechanism).

In addition, the when flap valve 330 is in the position illustrated by FIG. 8b, conduits 314 and 316 (not shown) are blocked off to prevent retrograde suction of sealant agents 318 and 320. Such blocking can be facilitated through the pinching of conduits 314 and 316 that consummates with the actuation of flap valve 330.

Figure 9A:
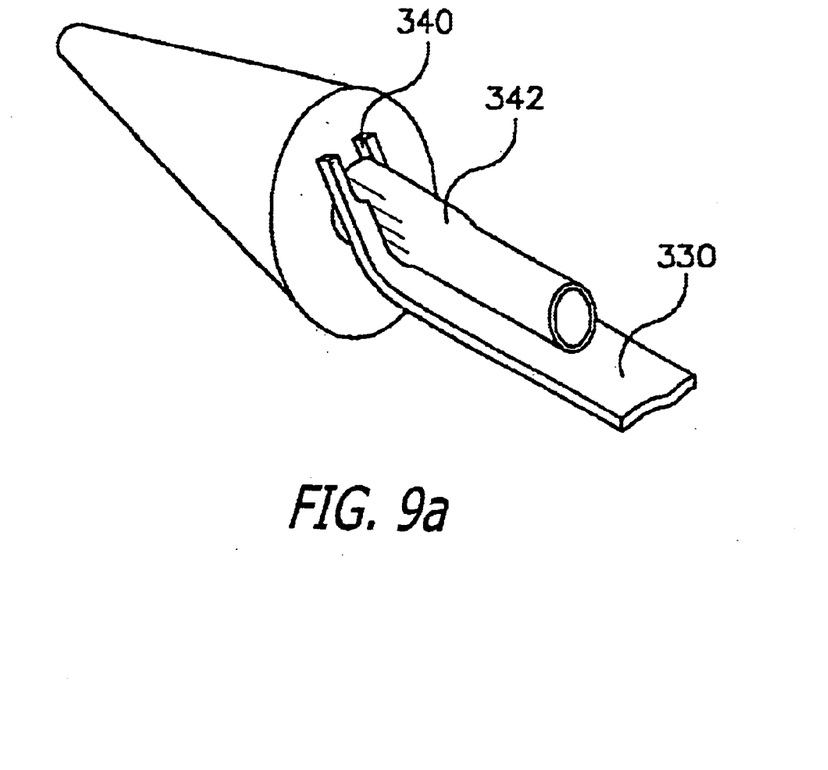
FIGS. 9a–b is a cross sectional view of a fifth embodiment of the present invention.
Figure 9B:
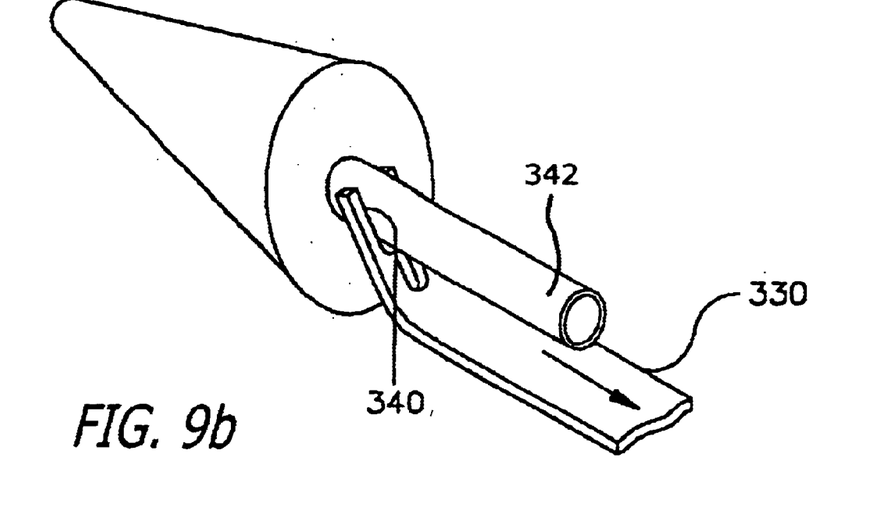

Alternatively, and as illustrated in FIGS. 9a and 9b conduit 342 can be a flexible silicone tube which is opened or closed through the use of a slidably secured shuttle 330. Shuttle 330 is equipped with an opening or slit 340 that reduces in size and therefore constricts flexible conduit 342 until it is effectively blocked off (as illustrated in FIG. 9a).

Movement of shuttle 330 may be achieved through the manipulation of a trigger ergonomic to manipulation of the user.

Effective closure of conduits 314 and 316 is facilitated, as discussed above, to prevent suction of agents 318 and 320 while clots are being removed from mixing chamber 312.

Figure 10A:
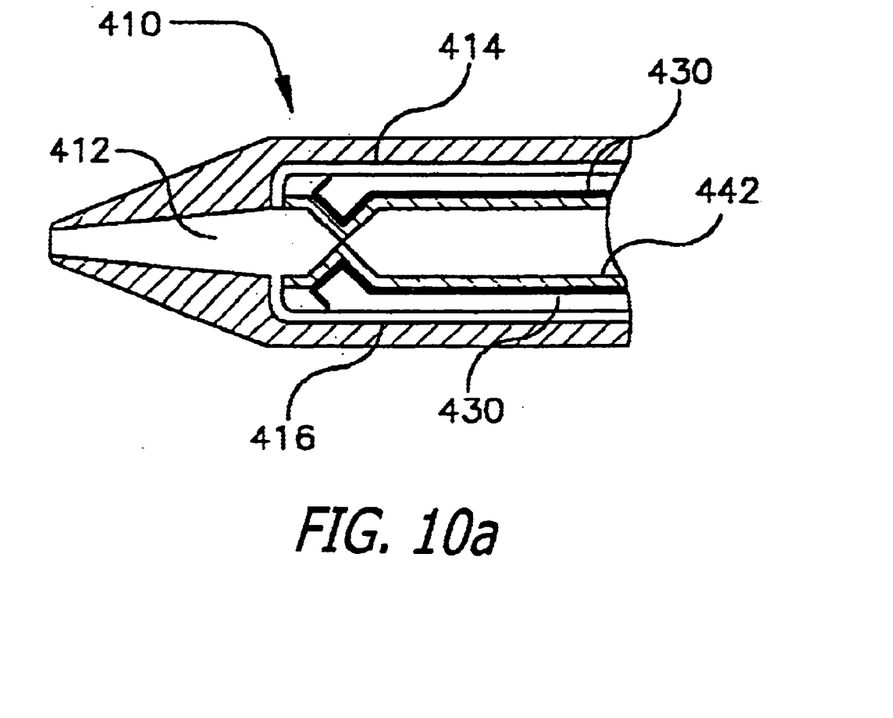
FIGS. 10a–b is a cross sectional view of a sixth embodiment of the present invention.

In yet another embodiment, tip 410 is provided with a dual action valve for blocking off of mixing chamber 412 from conduit 442. In this embodiment conduit 442 is a flexible silicone tube, and accordingly, the walls are capable of being manipulated by a pair of hinged pinching arms 430. As illustrated in FIG. 10a, arms 430 are hinged to flex the walls of silicon tube 442 inwardly. Thus, as arms 430 move inwardly, silicon tube 442 is compressed to effectively seal mixing chamber 412 from conduit 442.

Figure 10B:
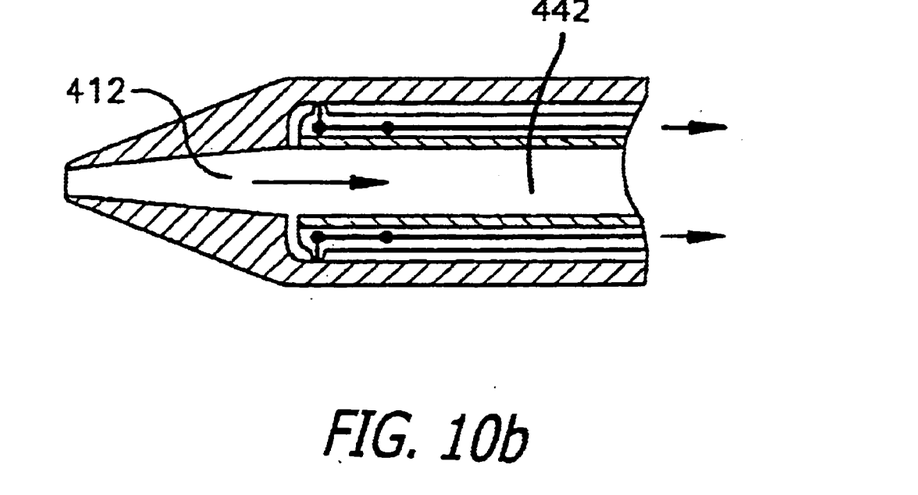

Once released, the resilient nature of silicon tube 442 causes conduit 442 to returns to its un-constricted position. In this position, retrograde clearing of area 412 is possible (FIG. 10b).

Effective closure of conduits 414 and 416 is facilitated, as discussed above, to prevent suction of agents 418 and 420 while clots are being removed from mixing chamber 412.

Figure 11A:
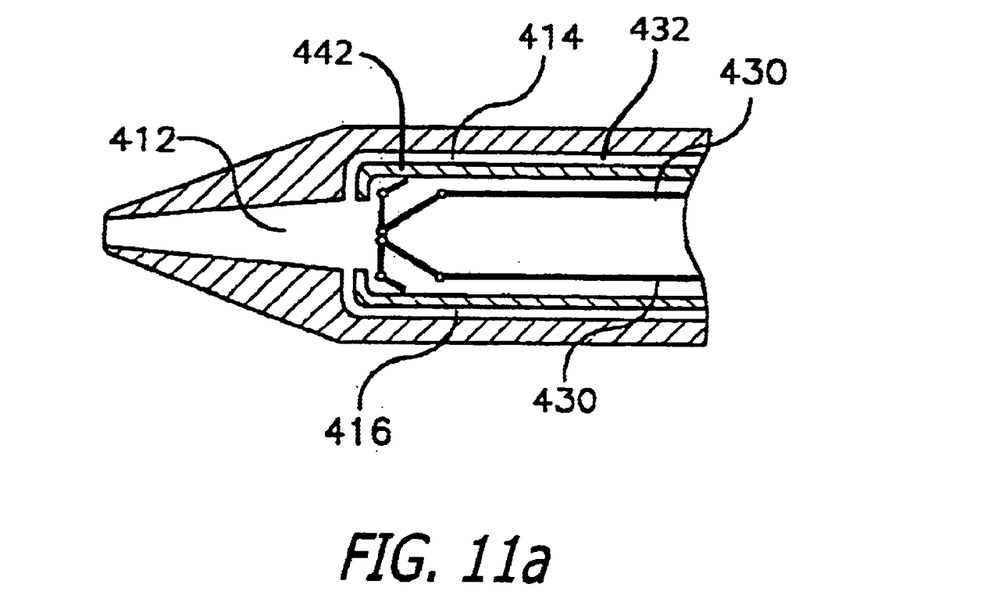
FIGS. 11a–b is a cross sectional view of a seventh embodiment of the present invention.
Figure 11B:
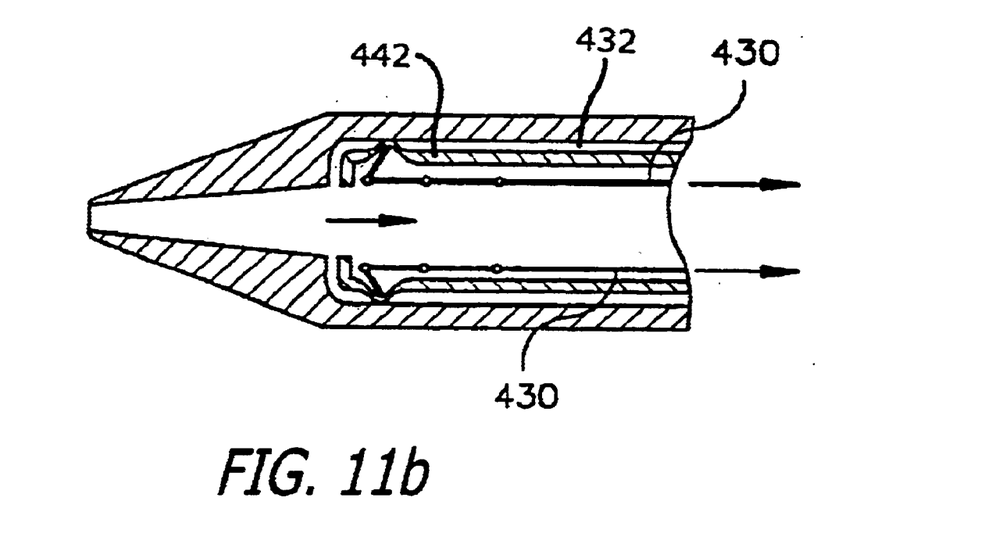

Alternatively, and as illustrated in FIGS. 11a and 11b, conduit 442 is a silicon tube and the outer wall of conduit 442 is positioned within shaft 432 to also define the area of conduits 414 and 416. Accordingly, the flexible wall of conduit 442 may be pinched outwardly by a pair of hinged arms 430 (FIG. 11b). In this position retrograde clearing of mixing chamber 412 is possible while also effectively blocking off conduits 414 and 416. Thus, suction can be applied to mixing chamber 412 without also sucking the agents out of conduits 414 and 416.

In addition, hinged arms 430 are also configured to block off conduit 442 from mixing chamber 412 (as illustrated in FIG. 11a).

Figure 12A:
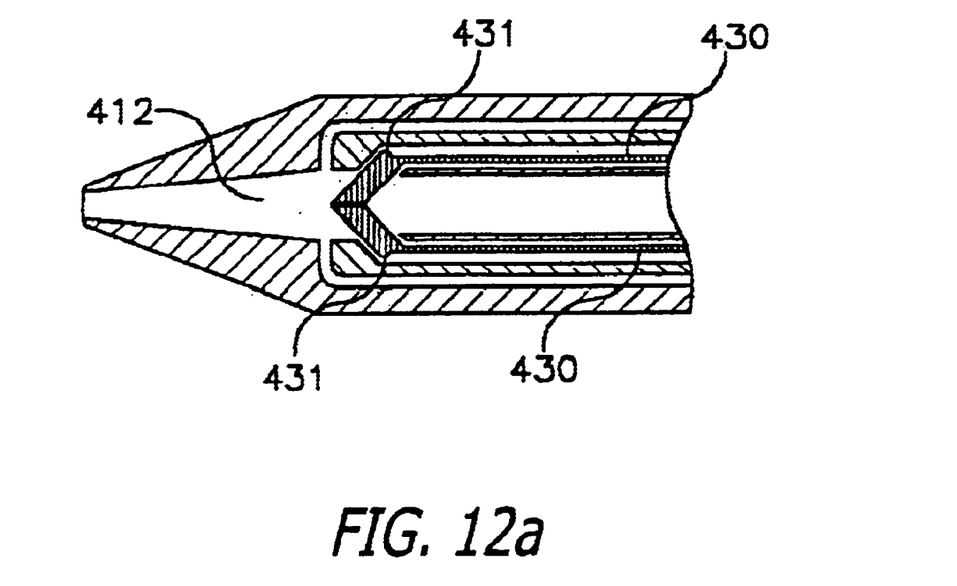
FIGS. 12a–b is a cross sectional view of an eighth embodiment of the present invention.
Figure 12B:
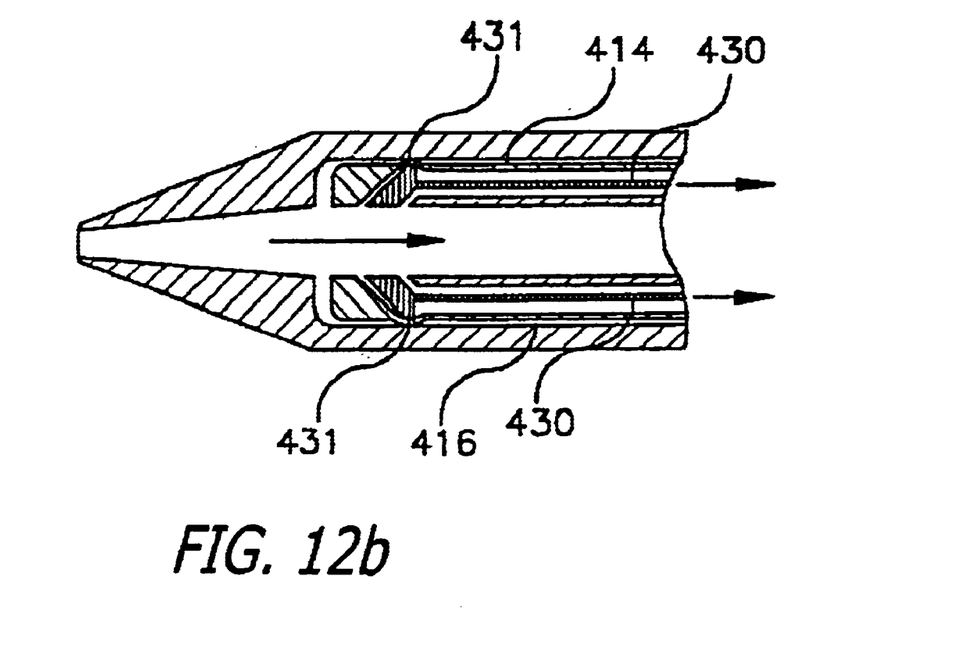

Alternatively, and as illustrated in FIGS. 12a and 12b, a pair of shuttles 430, each having a nub 431 for pinching flexible conduits 414 and 416, are positioned to allow for retrograde clearing while also pinching off conduits 414 and 416. In this embodiment the ends of shuttles 430 are angularly configured to slide backward while also constricting flexible conduits 414 and 416.

Figure 13A:
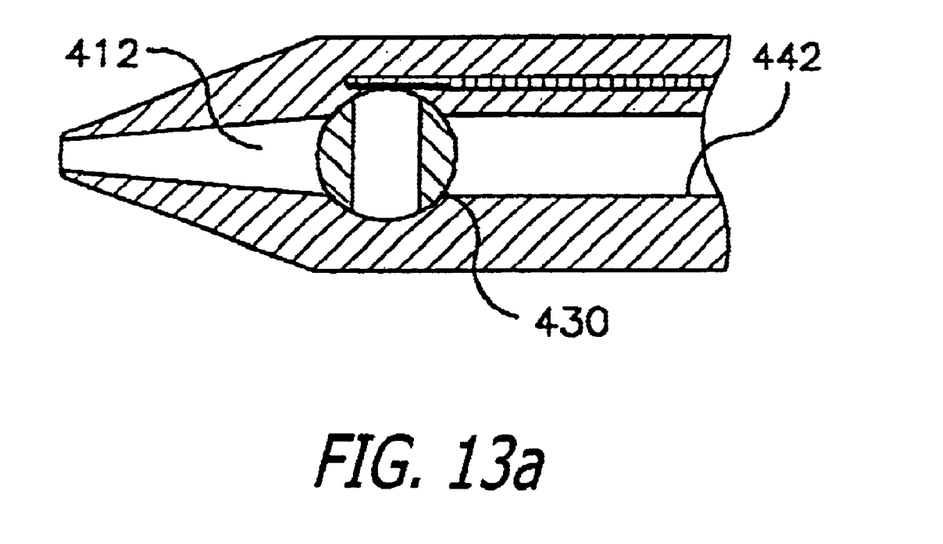
FIGS. 13a–b is a cross sectional view of a ninth embodiment of the present invention.
Figure 13B:
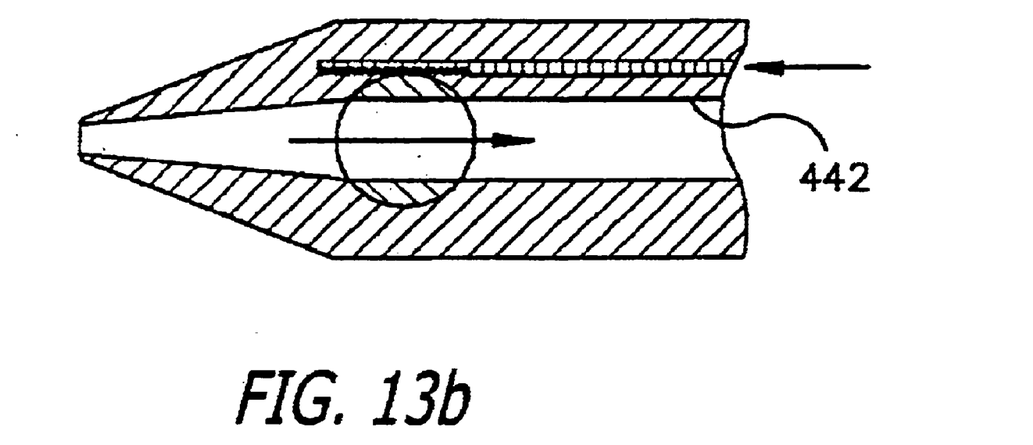

In yet another variation (FIGS. 13a and 13b), the communication of mixing chamber 412 and conduit 442 is regulated by a stop cock valve 430. Valve 430 is configured to block off conduits 414 and 416 when it is in its open position.

The present invention provides a novel surgical method of applying a quick coagulating sealant to unexposed or internal biological surfaces, e.g. human or animal anatomical surfaces, that are remotely accessible while also providing for retrograde clearing of the application device.

Thus, a surgeon, or other user, can insert the applicator tip into a cavity in a subject, operate applicator to disperse sealant and to apply the sealant to desired locations in the subject cavity, withdraw the applicator and manipulate it to a clearing configuration, apply suction to clear away any clogs and, if desired, reinsert the applicator to apply further sealant.

Moreover, the user can remotely control the release of the sealant and/or the sealant components by way of the mechanical components illustrated and described in the instant application.

In addition, alternative embodiments of the present invention also allow for the applicator to be manipulated to a clearing configuration without having to remove the applicator tip.

While illustrative embodiments of the invention have been described above, it is, of course, understood that various modifications will be apparent to those of ordinary skill in the art. Such modifications are contemplated as being within the spirit and scope of the present invention which is limited and defined only by the appended claims.

What is claimed is:

1. A fluid application tip for use with a handheld fluid applicator for selectively applying multiple fluids to a work surface, the applicator tip comprising:
   a) a mixing chamber;
   b) at least one cannula through which fluid can be dispensed from the mixing chamber;
   c) a suction pathway to provide suction to said mixing chamber;
   d) a pair of conduits providing fluids to said mixing chamber; and
   e) an operable control valve to control the coupling of said suction pathway and said pair of conduits to said mixing chamber, said control valve coupling said suction pathway to said mixing chamber when said control valve is in a first position and said control valve coupling said pair of conduits to said mixing chamber when said control valve is in a second position, said control valve being remotely operable by a manual actuator.

2. An applicator tip as in claim 1, wherein said control valve is a rotatably mounted disk being mounted for rotation into said first and second positions.

3. An applicator tip as in claim 1, further comprising a pair of one way valves being positioned to only allow fluids to flow from said conduits into said mixing chamber.

4. An applicator tip according to claim 1 comprising separate cannulas for simultaneously for applying suction and fluids to a work surface.

5. An applicator tip as in claim 1 wherein the fluid being dispensed from said mixing chamber is sealant agent comprising at least two individual sealant agent components where the components are supplied to said mixing area by said pair of conduits.

6. An applicator tip as in claim 1, wherein said control valve is a shuttle valve having a valve opening and said shuttle valve being configured, dimensioned and positioned to slidably position said valve opening into said first and second positions.

7. An applicator tip as in claim 1, wherein said pair of conduits further comprise a flexible membrane, said flexible membrane defining an inner and outer wall of said pair of conduits.

8. An applicator tip as in claim 7, wherein said control valve constricts said flexible membrane when said control valve is in said first position causing said inner walls of said flexible membrane to move closer together and effectively block off said pair of conduits.

9. An applicator tip as in claim 1, wherein said control valve is a flap valve being mounted for movement into said first and second positions.

10. An applicator tip as in claim 8, wherein said control valve is manipulated from a position remote from said applicator tip.

11. An applicator tip as in claim 9, wherein said control valve is manipulated to control the flow of fluids from said conduits.

12. An applicator tip as in claim 11, wherein said control valve is manipulated from a position remote from said applicator tip.

13. An applicator tip according to claim 1 wherein said applicator tip is capable of coupling to a fluid applicator.

* * * * *